(12) United States Patent
Johnson

(10) Patent No.: US 8,702,667 B1
(45) Date of Patent: Apr. 22, 2014

(54) MALE INCONTINENCE GARMENT

(71) Applicant: Gwendel Johnson, Berea, KY (US)

(72) Inventor: Gwendel Johnson, Berea, KY (US)

(*) Notice: Subject to any disclaimer, the term of this patent is extended or adjusted under 35 U.S.C. 154(b) by 0 days.

(21) Appl. No.: 13/680,802

(22) Filed: Nov. 19, 2012

Related U.S. Application Data

(60) Provisional application No. 61/742,308, filed on Aug. 8, 2012.

(51) Int. Cl.
  *A61F 13/15* (2006.01)
  *A61F 5/44* (2006.01)

(52) U.S. Cl.
  USPC .............. 604/385.09; 604/385.03; 604/349

(58) Field of Classification Search
  USPC ............ 604/327, 394, 385.09, 395, 343, 347,
      604/349–353, 385.03, 385.04, 385.14,
      604/385.19, 386, 387, 396; 2/54, 403, 404,
      2/405; 602/67, 68
  See application file for complete search history.

(56) References Cited

U.S. PATENT DOCUMENTS

| | | | | |
|---|---|---|---|---|
| 2,595,507 | A * | 5/1952 | Beck ............................. | 604/395 |
| 3,366,116 | A * | 1/1968 | Huck ............................ | 604/347 |
| 4,195,630 | A * | 4/1980 | Connery et al. ................ | 602/67 |
| 4,637,078 | A * | 1/1987 | Southwell ...................... | 2/408 |
| 4,961,419 | A * | 10/1990 | Tribble et al. ................... | 602/70 |
| 5,074,853 | A | 12/1991 | Bryant | |
| 5,283,912 | A * | 2/1994 | Chung ............................. | 2/403 |
| 5,569,229 | A * | 10/1996 | Rogers ..................... | 604/385.09 |
| 5,649,913 | A * | 7/1997 | Cohen ........................... | 604/353 |
| 5,716,350 | A * | 2/1998 | Ryan ........................ | 604/385.09 |
| 5,875,495 | A * | 3/1999 | Thrower .......................... | 2/403 |
| 5,984,910 | A * | 11/1999 | Berke ............................. | 604/352 |
| 6,007,524 | A * | 12/1999 | Schneider ..................... | 604/327 |
| 6,132,412 | A | 10/2000 | Jones | |
| 6,197,011 | B1 | 3/2001 | Freitas et al. | |
| 6,662,378 | B2 * | 12/2003 | Vartanyan ........................ | 2/403 |
| 6,817,992 | B1 * | 11/2004 | Sassak et al. ............ | 604/385.09 |
| RE39,371 | E * | 10/2006 | Johnson ....................... | 604/327 |
| 7,434,273 | B2 * | 10/2008 | Chung ............................ | 2/403 |
| 7,815,619 | B2 | 10/2010 | Miskie | |
| D651,377 | S * | 1/2012 | Weaver et al. ................. | D2/712 |
| D660,551 | S * | 5/2012 | Steele ............................ | D2/712 |
| 8,187,238 | B1 | 5/2012 | Dupree | |

(Continued)

FOREIGN PATENT DOCUMENTS

| | | |
|---|---|---|
| CH | 694 519 A5 | 3/2005 |
| FR | 2 701 389 A1 | 8/1994 |

(Continued)

*Primary Examiner* — Lynne Anderson
*Assistant Examiner* — Bradley Philips
(74) *Attorney, Agent, or Firm* — Pearne & Gordon LLP

(57) ABSTRACT

Male incontinence garment structures and methods of use are provided. The garment includes an undergarment defining an interior space and an exterior space. An aperture enables the penis of the wearer to extend through the aperture from the interior space to the exterior space. A flap at least partially covers the aperture and is selectively movable between an open position and a closed position. A pouch is located between the flap in the closed position and the undergarment. In a further example, a pad is configured to be placed within the pouch and confine the penis as it extends from the interior space of the undergarment, through the aperture, and into the pad. A method includes placing the undergarment about the body of the male incontinence garment wearer, placing the penis of the male incontinence garment wearer through the aperture and the hole into the pad.

8 Claims, 2 Drawing Sheets

(56) References Cited

U.S. PATENT DOCUMENTS

| | | |
|---|---|---|
| 2002/0177825 A1 | 11/2002 | Scovel |
| 2003/0028161 A1* | 2/2003 | Carballo ................. 604/349 |
| 2004/0106909 A1 | 6/2004 | Browning |
| 2011/0077610 A1 | 3/2011 | Kikumoto et al. |

FOREIGN PATENT DOCUMENTS

| | | |
|---|---|---|
| FR | 2 822 057 A1 | 9/2002 |
| JP | 11-216155 A | 8/1999 |
| JP | 2007089778 A | 4/2007 |
| WO | 98/48753 A1 | 11/1998 |

* cited by examiner

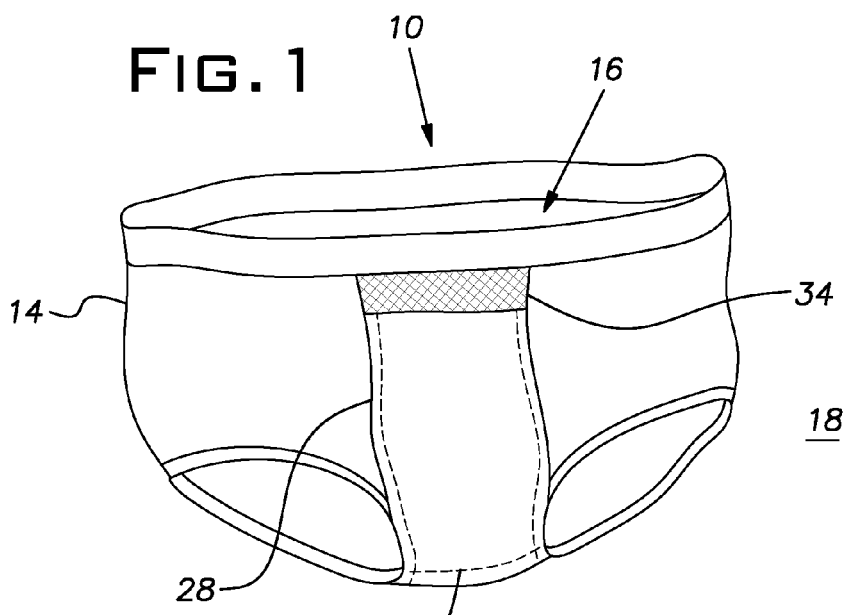
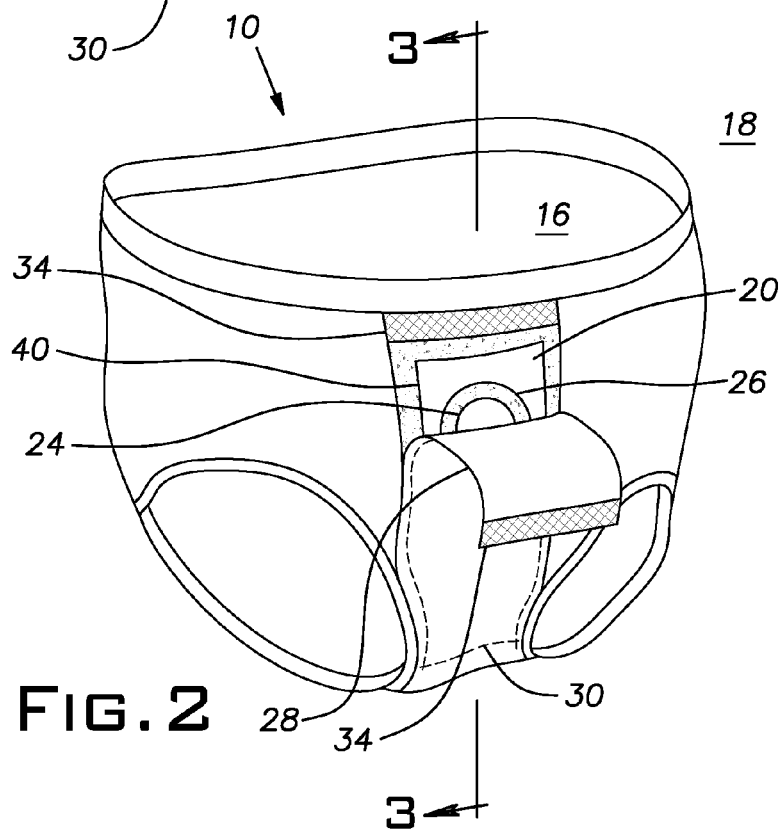

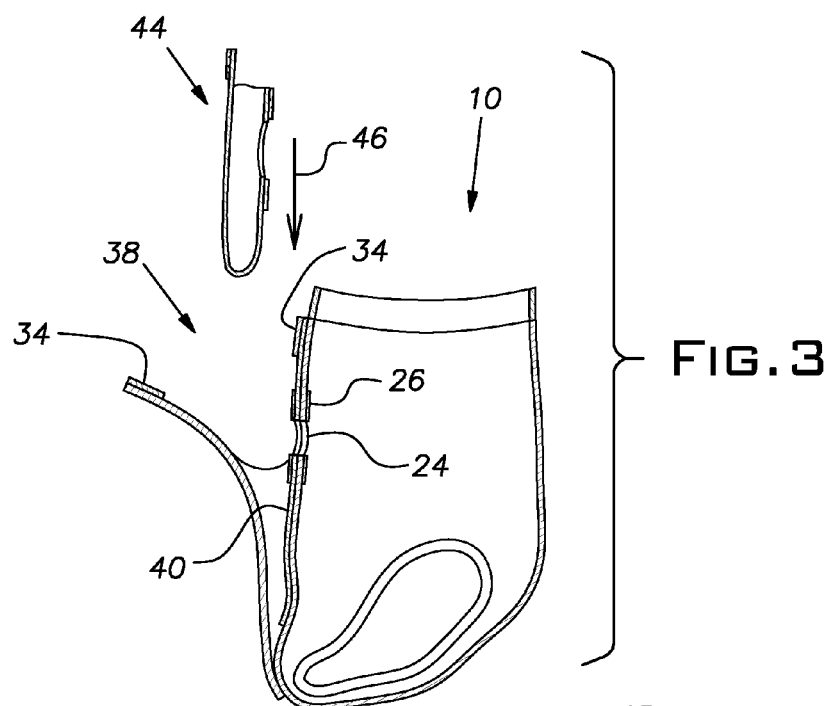
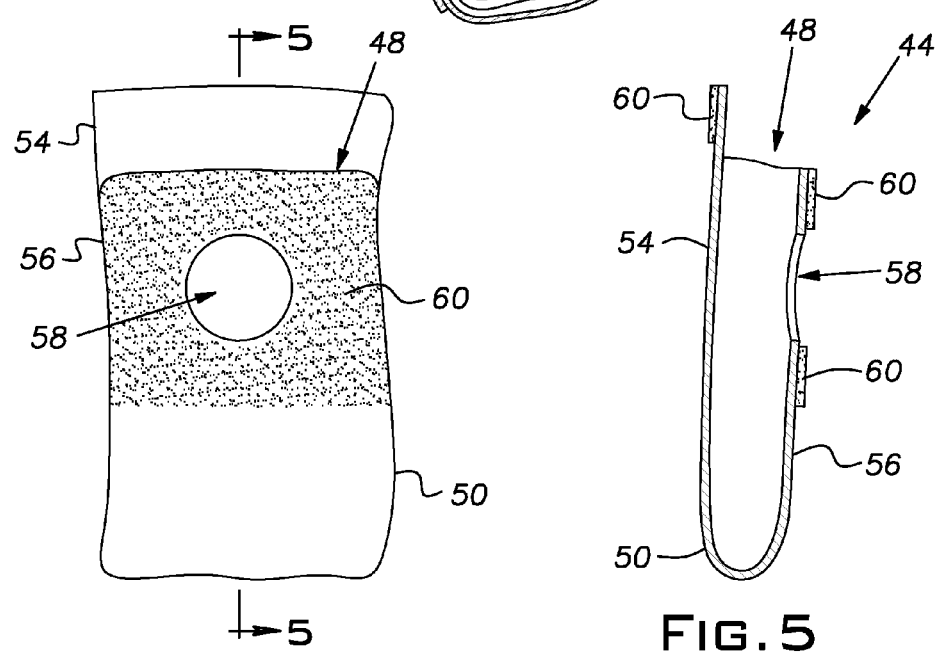
FIG. 3
FIG. 4
FIG. 5

MALE INCONTINENCE GARMENT

This application claims the benefit of U.S. Provisional Application No. 61/742,308, filed Aug. 8, 2012, the entire disclosure of which is hereby incorporated herein by reference.

BACKGROUND OF THE INVENTION

1. Field of the Invention

The invention relates to male incontinence devices, and specifically relates to male incontinence devices with external receptacles for male genitalia and urine.

2. Discussion of Prior Art

Males having urinary incontinence often wear devices and undergarments to accept and contain urine. Many of these devices and undergarments can be awkward to apply or use. Other devices are readily apparent to others that may see the device or undergarment, creating embarrassment for the wearer. Still more devices do not provide ease of use when the wearer is able to control his flow of urine and can urinate into a typical receptacle or fixture as done by the majority of males. Furthermore, many of the existing devices and undergarments designed for male incontinence issues involve disposing of the entire device or undergarment after urine is collected within the device or undergarment. Accordingly, it would be beneficial to provide a male incontinence garment that provides an ease and familiarity of application for the wearer, and appears to others as a typical men's undergarment. Additionally, it would also be beneficial to provide a male incontinence garment that is easily used during situations when the user is able to control his flow of urine into typical fixtures, and minimizes the amount of disposable material within the garment.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

A male incontinence garment comprising an undergarment. The undergarment defines an interior space and an exterior space. The undergarment includes an aperture configured to enable the penis of a male incontinence garment wearer to extend through the aperture from the interior space of the undergarment to the exterior space of the undergarment. The male incontinence garment also includes a flap located in the exterior space to at least partially cover the aperture. The flap is selectively movable between an open position and a closed position. The flap and the undergarment together define a pouch located between the flap in the closed position and the undergarment. The pouch is configured to confine the penis of a male incontinence garment wearer as the penis extends from the interior space of the undergarment, through the aperture, and into the pouch.

A male incontinence garment comprising an undergarment. The undergarment defines an interior space and an exterior space. The undergarment includes an aperture configured to enable the penis of a male incontinence garment wearer to extend through the aperture from the interior space of the undergarment to the exterior space of the undergarment. The male incontinence garment also includes a flap located in the exterior space to at least partially cover the aperture. The flap is selectively movable between an open position and a closed position. The flap and the undergarment together define a pouch located between the flap in the closed position and the undergarment. The male incontinence garment further includes a pad configured to be placed within the pouch. The pad is also configured to confine the penis of a male incontinence garment wearer as the penis extends from the interior space of the undergarment, through the aperture, and into the pad.

A method for using a male incontinence garment. The method comprises the step of providing a male incontinence garment including an undergarment. The undergarment defines an interior space and an exterior space. The undergarment includes an aperture configured to enable the penis of a male incontinence garment wearer to extend through the aperture from the interior space of the undergarment to the exterior space of the undergarment. The male incontinence garment also includes a flap located in the exterior space to at least partially cover the aperture. The flap is selectively movable between an open position and a closed position. The flap and the undergarment together define a pouch located between the flap in the closed position and the undergarment. The male incontinence garment further includes a pad configured to be placed within the pouch. The pad is also configured to confine the penis of a male incontinence garment wearer as the penis extends from the interior space of the undergarment, through the aperture, and into the pad. The method also includes placing the undergarment about the body of the male incontinence garment wearer so that the undergarment covers the crotch area of the body. The method further includes placing the penis of the male incontinence garment wearer through the aperture into the pouch. The method still further includes placing the penis of the male incontinence garment wearer through the hole into the pad. The method also includes opening the pouch upon a detected sensation to urinate. The method further includes removing the penis from the pad to urinate and placing the penis into the pad upon completion of urination. The method still further includes closing the pouch. The method also includes removing the penis from the pad after urinating into the pad. The method further includes removing the pad from the pouch after urination. The method still further includes inserting a replacement pad into the pouch prior to the next urination.

BRIEF DESCRIPTION OF THE DRAWINGS

The foregoing and other aspects of the invention will become apparent to those skilled in the art to which the invention relates upon reading the following description with reference to the accompanying drawings, in which:

FIG. 1 is a front view of an example male incontinence garment including a flap according to at least one aspect of the present invention;

FIG. 2 is a perspective view of the male incontinence garment from FIG. 1 showing the flap in an open position;

FIG. 3 is a cross-section view of the male incontinence garment taken along line 3-3 in FIG. 2 illustrating the insertion of a pad;

FIG. 4 is a front view of the pad of FIG. 3; and

FIG. 5 is a cross-section view of the pad taken along line 5-5 in FIG. 4.

DETAILED DESCRIPTION OF THE INVENTION

Example embodiments that incorporate one or more aspects of the invention are described and illustrated in the drawings. These illustrated examples are not intended to be a limitation on the invention. For example, one or more aspects of the invention can be utilized in other embodiments and even other types of devices. Moreover, certain terminology is used herein for convenience only and is not to be taken as a limitation on the invention. Still further, in the drawings, the same reference numerals are employed for designating the same elements.

An example embodiment of a male incontinence garment 10 is shown in FIG. 1. The male incontinence garment 10 includes an undergarment 14. While the undergarment 14 is shown in a form similar to undergarments known as fly-front briefs, this depiction is not meant to be limiting on the present disclosure, and the undergarment can be similar to other types of undergarments such as no-fly briefs, boxers, boxer-briefs, etc. The undergarment 14 defines an interior space 16 and an exterior space 18. The undergarment 14 can also include a front panel 20 located such that a front panel 20 (best seen in FIG. 2) is located on the front side of a male wearer of the male incontinence garment 10. As with typical designs of human undergarments, the undergarment 14 can be designed and/or tailored to provide a particular level of comfort and allow a particular range of motion for the wearer of the undergarment 14.

In one example, the undergarment 14 can be designed to aesthetically appear as a typical pair of men's underwear, such that a casual observer of the undergarment 14 would not be able to differentiate the undergarment 14 from a typical pair of men's underwear. Additionally, the undergarment 14 can be constructed of materials that are standard materials in men's underwear. Designs such as these can help to alleviate and/or eliminate any embarrassment that the wearer of the male incontinence garment 10 may experience in situations when the male incontinence garment 10 is visible to others. In one example, the undergarment 14 is reusable and washable, enabling the undergarment 14 to be laundered as a typical pair of men's underwear. The undergarment 14 can be manufactured to enable the wearer or others to wash and re-use the undergarment 14 for about the same lifespan as a typical pair of men's underwear. In one example, this can include a range of at least about 150 to about 300 washing operations over the lifespan of the undergarment 14.

Turning to FIG. 2, the undergarment 14 includes an aperture 24. The aperture 24 is located in the front panel 20 and can be located in a position such that when the male incontinence garment 10 is worn by a male wearer, the aperture 24 is adjacent or within a relatively short distance of the wearer's penis. Both the size and location of the aperture 24 are designed to enable the penis of a male incontinence garment wearer to extend through the aperture 24 from the interior space 16 of the undergarment 14 to the exterior space 18 of the undergarment 14. In one example, the aperture 24 can be circular or nearly circular as shown in FIG. 2, however, other aperture shapes are also contemplated. For example, the aperture 24 can be in the shape of a channel, or overlapping segments of material similar to a fly in a typical pair of men's underwear.

The undergarment 14 can be designed to fit the male wearer's body so that after the wearer's penis is placed through the aperture, the penis is able to assume its natural hanging position. In this position, the front panel 20 separates the penis from the remainder of the wearer's skin and body, including the testicles and scrotum. In this position, the front panel 20 helps to eliminate or substantially eliminate contact and extended contact of urine expelled through incontinence with the skin and body of the wearer. Separation of urine from the skin and body of the male incontinence garment 10 can be beneficial, as extended contact of urine with human skin can negatively affect the health of the skin and the wearer of the male incontinence garment 10.

In one example, the front panel 20 can include reinforcement around the aperture 24. The reinforcement can be an elastic band 26 that is configured to surround the circumference of the penis of the male incontinence garment wearer. Reinforcement such as the elastic band 26 can help hold the penis in place and help reduce or eliminate undesired removal of the penis from the aperture 24. Elasticity of the elastic band 26 is selected so that the elastic band 26 provides a relatively low tension force about the circumference of the penis. A relatively low tension force about the circumference of the penis helps reduce or eliminate any discomfort to the wearer. Additionally, the relatively low tension force helps reduce or eliminate any restriction of urine flow through the urethra. Furthermore, the elastic band 26 can help reduce or eliminate the passage of urine from the exterior space 18 to the interior space 16 where it can contact the skin of the wearer. In one example, the penis is placed substantially entirely through the aperture 24 such that the elastic band 26 is located at the base of the penis, i.e., where the penis meets the body of the wearer.

The male incontinence garment 10 also includes a flap 28 located in the exterior space 18. The flap 28 can be a single flap attached to the front of the undergarment 14 relative to the area where the penis typically meets the inner facing of a typical pair of men's underwear. Similar to the undergarment 14, the flap 28 can be constructed of materials that are standard materials in men's underwear. Furthermore, the flap 28 can be attached to the front of the undergarment 14 using methods and materials that are used in typical men's underwear designs. For example, the flap 28 can be attached to the undergarment 14 by top stitching in a U-shaped pattern 30 around the at least a portion of the perimeter of the flap 28 as shown in FIGS. 1 and 2. The U-shaped pattern 30 is one example of an attachment pattern for the flap 28 and is not meant to be limiting. Furthermore, attachment structures other than stitching the pieces together can be used to attach the flap 28 to the undergarment 14. Both the material and attachment designs for the flap 28 help enable the male incontinence garment 10 to look like and be laundered like typical men's underwear as has been previously described.

The flap 28 is designed to at least partially cover the aperture 24, and in one example, the flap 28 entirely covers the aperture 24. The flap 28 is selectively movable between an open position as shown in FIG. 1 and a closed position as shown in FIG. 2. When the flap 28 is in the open position, the wearer of the male incontinence garment 10 has ready access to the aperture 24 in order to place his penis through the aperture 24 and/or remove his penis from the aperture 24. Furthermore, while wearing the male incontinence garment 10 and placing the flap 28 in the open position, the wearer can urinate normally into a typical fixture such as a urinal or a toilet in the case that the wearer senses the need to urinate and can access a fixture before he is incontinent. It is to be understood that the U-shaped pattern 30 of flap attachment is designed so that the flap 28 can be opened far enough to provide adequate access to the penis as is necessary.

In order to maintain the flap 28 in the closed position as desired, a fastening device 34 can be located on the flap 28 and at a corresponding location on the undergarment 14. In one example, the fastening device 34 can be a hook and loop fastener, although other fastening devices are also contemplated. As shown in FIG. 2, the fastening device 34 can be a strip of a hook and loop fastener attached to the top edge 36 of the flap 28. A corresponding strip of hook and loop fastener can be attached to the front panel 20 so that the two strips come into mating contact as the flap 28 is placed into the closed position and can be reliably connected with speed and minimum effort and/or skill by the wearer. Additionally, the hook and loop fasteners provide a fastening structure that is easily operated by those having minimal or reduced dexterity and/or strength. In one example, the width of the hook and loop fastener at the top of the flap 28 is about ½-inch.

Turning to FIG. 3, the flap 28 and the undergarment 14 together define a pouch 38 located between the flap 28 in the closed position and the undergarment 14. As can be appreciated, depending upon the attachment pattern of the flap 28, a portion of the pouch 38 can be defined between the flap 28 and the undergarment 14 even when the flap 28 is in the open position. The pouch 38 is configured to confine the penis of a male incontinence garment wearer as the penis extends from the interior space 16 of the undergarment 14, through the aperture 24, and into the pouch 38. The overall shape of the pouch 38 can conform to the shape of the wearer's body in order to be comfortable and help the male incontinence garment 10 be as inconspicuous as possible. Additionally, the overall shape of the pouch 38 can also be designed to limit the movement of the penis while it is confined to the pouch 38 of the male incontinence garment 10.

The pouch 38 is intended to contain moisture and reduce wetness for the wearer of the male incontinence garment 10. The containment feature of the male incontinence garment 10 helps reduce and/or eliminate the passage of urine passed incontinently to undesired locations such as to the interior space 16 of the undergarment 14, to the clothing of the wearer, down the legs of the wearer, and any other location. Containing incontinent urine for the wearer provides not only a greater level of sanitary health, but also can promote confidence in the wearer and help eliminate embarrassment due to incontinence that can be detected by others.

In order to help contain urine within the pouch 38, the pouch 38 can include an anti-microbial, liquid resistant fabric 40. In one example, the anti-microbial, liquid resistant fabric 40 can be attached to the front panel 20 of the undergarment 14 such that the anti-microbial, liquid resistant fabric 40 faces the interior of the pouch 38. Similarly, anti-microbial, liquid resistant fabric 40 can be attached to the flap 28 to face the interior of the pouch 38. Alternatively and/or additionally, the flap 28 and/or the front panel 20 can be composed of the anti-microbial, liquid resistant fabric 40. Any combination of these construction possibilities are contemplated. The anti-microbial, liquid resistant fabric 40 can promote sanitary health and limit or eliminate passage of urine from the pouch 38 to undesired locations as described above.

The male incontinence garment 10 can also include a pad 44 configured to be placed within the pouch 38 as illustrated by arrow 46 in FIG. 3. Turning now to FIG. 4, the pad 44 includes a material that contains moisture. For the purposes of this disclosure, a material that contains moisture can be defined as a moisture-absorbent material that can hold moisture such as human urine within the confines of the material to substantially limit or even eliminate contact of expelled urine with the wearer's skin and garments. In a further example, the moisture absorbent material can be composed of numerous types of materials including, but not limited to, cellulosic fluff pulp, tissue layers, air-laid materials, highly absorbent polymers (so-called superabsorbents), absorbent foam materials, absorbent nonwoven materials or the like. In one example, the pad 44 can absorb several times its own weight in liquid (e.g., urine). Additionally, the pad 44 can be designed to contain at least the average amount of incontinent urine from an adult male during one urination. In a more particular example, the pad 44 can be designed to contain at least the average amount plus a predetermined amount of incontinent urine from an adult male during one urination.

The configuration of the pad 44 can form a pocket 48. The pocket 48 can be formed in any of a number of methods as are known in the art. In one example, the pad 44 is formed by a single sheet 50 of moisture-absorbent material folding a first portion 54 of the single sheet 50 over a second portion 56 of the single sheet 50. At least some length of the seams of the first portion 54 and the second portion 56 can be heat sealed and pressed together to form the pocket 48. In one example, the first portion 54 can be longer in comparison to the second portion 56. As shown in the cross-section view of FIG. 5, the pad 44 can form a U-shaped pocket as the first portion 54 is folded over the second portion 56. As best seen in FIG. 3, the longer first portion 54 of the pad 44 can face the flap 28, and the shorter second portion 56 can face the front panel 20 of the undergarment 14. In one example, the open end of the pocket 48 is oriented substantially upward with the pocket 48 having a closed end at the bottom.

The second portion 56 of the pad 44 can include a hole 58, wherein the penis passes through the hole 58 into the pocket 48 formed by the pad 44. As described above, the penis can extend from the interior space 16, through the aperture 24, and into the pouch 38. The penis can then be placed through the hole 58 and into the pocket 48. As with the pouch 38, the pocket 48 can be designed to fit the male wearer's body so that after the wearer's penis is placed through the hole 58, the penis is able to assume its natural hanging position. In FIG. 5, the penis (not shown) passes through the hole 58 on the right side and hangs toward the bottom of the figure. The pocket 48 is configured to accept and confine the penis and urethra of the male incontinence garment wearer. Similar to the design of the pouch 38, the confinement of the penis to the pocket 48 separates the penis and urine from the skin and body of the wearer in order to improve sanitary health for the wearer. Additionally, the confinement of the penis within the pocket 48 and the pouch 38 helps hold any incontinent urine and/or other fluids within the moisture-absorbent pad 44 and the pouch 38. The combination of the moisture-absorbent material in the pad 44 and the anti-microbial, liquid resistant fabric 40 in the pouch 38 can limit or eliminate liquid and/or moisture leakage from the pouch 38 to undesired locations as previously described. In fact, the pad 44 can be an autonomous, stand-alone moisture containing environment to accommodate the penis of the wearer and contain any moisture from urine leakage due to incontinence. The urine is prevented from contacting the skin of the user by containing it within the pad 44 or alternately, within the pad 44 and the pouch 38.

Returning to FIG. 4, the pad 44 further includes an adhesive 60, represented by cross-hatching. The adhesive 60 is configured to secure at least a portion of the pad 44 to the undergarment 14. In one example, the adhesive 60 can be placed on an area at the lower end of the second portion 56, and this adhesive 60 can help secure the pad 44 to the front panel 20. The adhesive 60 is located to avoid any areas that may be in contact with the wearer's penis, hair, or other sensitive areas that may provide discomfort. Additionally, adhesive 60 can also be applied to the side of the pad 44 that contacts the flap 28 (best seen in FIG. 2). In one example, the adhesive 60 can be applied for a determined width along the top edge of the first portion 54. During use, the adhesive 60 can contact the top portion of the flap 28 and secure the pad 44 to the flap 28. As previously described, there may be times when the wearer can detect the urge to urinate and is able to reach a typical fixture designed to receive urine. In this case, the wearer can address the fixture, arrange outerwear as needed, and place the flap 28 in the open position. As the flap 28 is placed in the open position, the adhesive 60 enables a length of the first portion 54 of the pad 44 to move in concert with the flap 28, thereby providing access to the wearer's penis. The wearer is then able to urinate into the receptacle in the same manner of men wearing typical men's underwear. In one example, the width of a strip of the adhesive 60 mating with the flap 28 is about ½-inch, adjacent or below the ½-inch strip of hook and loop fastener previously described. This arrangement enables the wearer or a helper to open the flap 28 and access the pad 44 within the pouch 38 without contacting any surfaces that may be wet.

The adhesive 60 can be any of the many adhesives that are known in the art. Additionally, prior to placement within the pouch 38, the adhesive 60 may be covered by an adhesive backing (not shown) as is known in the art. Prior to final placement within the pouch, the wearer or a helper can remove the adhesive backing and attach the pad 44 to structure making up the pouch 38 such as the flap 28 and the front panel 20. Removal of the adhesive backing can take place after the wearer has placed his penis through the aperture 24 and through the hole 58 and the pad 44 is correctly positioned within the pouch 38. In one example, the adhesive 60 provides suitable force to keep the pad 44 in a desired location while also being relatively easy to remove the pad 44 and the adhesive 60. As such, the pad 44 and the adhesive 60 are selectively removable from the male incontinence garment 10 as desired and replaced with a fresh, unused pad 44. In one example, the pad 44 is disposable, and the wearer can simply discard the used pad.

Should the wearer choose, the male incontinence garment 10 as described can be used with or without other male incontinence devices as are known in the art, such as clip devices. The present disclosure can provide additional comfort to the wearer of the male incontinence garment 10 as the clip device can be placed in the pouch 38, away from the testicles, skin of the groin area, hair, and other areas of the body. Use of the clip device can be with or without the pad 44.

Methods for using a male incontinence garment will now be described. One example method includes the step of providing a male incontinence garment as previously described. The male incontinence garment includes an undergarment defining an interior space and an exterior space. The undergarment includes an aperture configured to enable the penis of a male incontinence garment wearer to extend from the interior space of the undergarment to the exterior space of the undergarment. The male incontinence garment also includes a flap located in the exterior space to at least partially cover the aperture. The flap is selectively movable between an open position and a closed position. The flap and the undergarment together define a pouch located between the flap in the closed position and the undergarment. The male incontinence garment also includes a pad configured to be placed within the pouch. The pad confines the penis of a male incontinence garment wearer as the penis extends from the interior space of the undergarment, through the aperture, and into the pad.

The method continues with the step of placing the undergarment about the body of the male incontinence garment wearer so that the undergarment covers the crotch area of the body. The male incontinence garment can be designed to fit about the wearer's body similar to typical men's underwear. The method continues with the step of placing the penis of the male incontinence garment wearer through the aperture into the pouch. The pouch is configured to confine the penis within the pouch to help limit and/or eliminate undesired leakage of urine from the pouch to the skin, clothing, or other body parts of the wearer.

The method continues with the step of placing the penis of the male incontinence garment wearer through the hole into the pad, wherein the pad confines the penis of a male incontinence garment wearer as the penis extends from the interior space of the undergarment, through the aperture, through the hole and into the pad. The pad can be moisture-absorbent and an autonomous, stand-alone moisture containing environment to accommodate the penis of the wearer containing any moisture from urine leakage due to incontinence. Urine is prevented from contacting the skin of the user by containing it within the pad or alternately, within the pad and the pouch.

The method can continue with the step of opening the pouch upon detected sensation to urinate. This step is helpful for the wearer of the male incontinence garment who may have the ability from time-to-time, or even the majority of times to detect his need to urinate and can reach a location where he can urinate as the majority of adult males do. In some cases, this may be when the wearer reaches a typical fixture such as a toilet or a urinal. The wearer can discreetly open his outer garments appropriately, and open the pouch. The arrangement of the pad inside the pouch enables the pocket of the pad to open with the opening of the pouch.

The method continues with the step of removing the penis from the pad to urinate so that the urine is not deposited into the pad. The typical process of male urination then ensues. The method then continues with the step of placing the penis into the pad upon completion of urination. After urination, the wearer can simply reinsert his penis into the pad which has remained dry and free of urine during the controlled urination of the wearer.

The method continues with the step of closing the pouch. The wearer can then simply close the pouch, and this controlled urination portion of the method can appear to a casual observer to be the wearer operating a typical male undergarment with no indication of incontinence-related features of the undergarment itself. With the arrangement of the male incontinence garment as described above, the step of closing the pouch will also close the pad so that the pocket formed by the pad accepts and confines the penis and urethra of the male incontinence garment wearer.

As can be appreciated, the wearer of the male incontinence garment may not always have the luxury of sensing the need to urinate or may not have the time to reach a typical fixture such as a toilet or a urinal. In these situations, the wearer may urinate into the pocket formed by the pad. The method continues with the step of removing the penis from the pad after urinating into the pad in the event that the wearer was incontinent. The method also includes the step of removing the pad from the pouch after urination into the pad. In one example, removal of the pad can occur as the pad reaches its absorbancy limit. In another example, removal of the pad can occur after every incontinence event. The pad can be disposable, and a typical wearer may expect to use about three to about six pads during an average day. The method can also include the step of inserting a replacement pad into the pouch prior to the next urination.

In another example of the method, the male incontinence garment further includes a fastening device located on the flap and at a corresponding location on the undergarment. The fastening device can be a strip of a hook and loop fastener attached to the top edge of the flap. A corresponding strip of hook and loop fastener can be attached to the front panel so that the two strips come into mating contact as the flap is placed into the closed position and can be reliably connected with speed and minimum effort and/or skill by the wearer. Additionally, the hook and loop fasteners provide a fastening structure that is easily operated by those having minimal or reduced dexterity and/or strength. In one example, the width of the hook and loop fastener at the top of the flap is about ½-inch.

In another example of the method, the pad forms a pocket, and the pocket accepts and confines the penis and urethra of the male incontinence garment wearer. Additionally, the pad can include a hole, wherein the penis passes through the hole into the pocket formed by the pad. The wearer or a helper can place the penis through the hole in the pad and into the pocket. The pocket accepts and confines the penis to limit movement of the penis and help limit the possibility of the penis leaving the pocket and/or the pouch.

In another example of the method, the pad further includes an adhesive configured to secure at least a portion of the pad to the undergarment. After the wearer or a helper places the penis through the hole of the pad, the adhesive backing is removed to positively locate the pad in a desired location in the pouch by applying a relatively low amount of force to urge the pad and corresponding parts together to engage the adhesive with the pouch components.

In another example of the method, the pad and the adhesive are selectively removable from the pouch. The arrangement of the adhesive enables the wearer or a helper to remove the pad and the adhesive with relatively little effort. Upon removal of a pad that has been soiled, the pad can be replaced with an unused pad, or the male incontinence garment can be laundered, after which an unused pad is placed into the pouch. After replacement of the pad, the male incontinence garment is in condition for subsequent use.

The described male incontinence garment and methods of use have several appreciable benefits which include, but are not limited to the following. The pouch located outside the interior space of the undergarment provides an enclosure to limit or eliminate undesired contact and/or extended contact of urine with the wearer's skin, outer garments, etc. The external pouch provides containment for moisture and/or liquid that benefits sanitary health and eliminates some possible embarrassment of the wearer to detectable incontinence. Another benefit is that the undergarment can appear to the casual observer as typical men's underwear, again saving the wearer from possible embarrassment of others learning of a wearer's incontinence problem. A further benefit can be an elimination of waste. The described male incontinence garment includes a relatively small disposable pad when compared to many known incontinence devices that can be equated to adult-sized diapers. These adult-sized diapers are typically designed for single use and require the entire device to be discarded. By comparison, the pad of the disclosed device eliminates much of the waste represented by adult-sized diapers. Yet another benefit is the ease of use of the described device during controlled urination. As previously described, the wearer, upon sensing the need to urinate, can approach a typical fixture, arrange his outer garments, place the flap in the open position and maneuver the penis to release urine into the fixture. The operation can be practically unnoticeable to others in the vicinity that the wearer might be in a special device designed for persons experiencing incontinence.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. A male incontinence garment comprising:
an undergarment, wherein the undergarment defines an interior space and an exterior space and the undergarment includes an aperture configured to enable the penis of a male incontinence garment wearer to extend through the aperture from the interior space of the undergarment to the exterior space of the undergarment,
wherein the undergarment includes a continuous waistband that is a permanent loop, and the undergarment defines two leg holes, wherein each leg hole is defined by a continuous border that is a permanent loop, the undergarment is configured to be worn as men's briefs;
a flap, wherein the flap is overlying the undergarment in the exterior space to at least partially cover the aperture, the flap being selectively movable between an open position and a closed position, the flap and the undergarment together defining a pouch located between the flap in the closed position and the undergarment, wherein the flap has a flap bottom and side portions and is attached to the undergarment at the bottom and at least upper edges of the side portions are not attached to the undergarment such that when the flap is in the open position, a wearer of the male incontinence garment has ready access to the aperture in order to place the penis through the aperture and/or remove the penis from the aperture while the undergarment remains in place; and
a removable pad, wherein the pad is configured to be placed within the pouch, and to confine the penis of a male incontinence garment wearer as the penis extends from the interior space of the undergarment, through the aperture, and into the pad, wherein the pad forms a pocket, the pocket having a closed end at the pocket bottom, wherein the pocket is configured to accept and confine the penis and urethra of the male incontinence garment wearer,
wherein the pad further includes an adhesive, wherein the adhesive is configured to secure at least a portion of the pad to the flap,
wherein as the flap is placed in the open position, the adhesive enables a length of a first portion of the pad to move in concert with the flap, thereby providing access to the penis while the undergarment remains in place.

2. The male incontinence garment according to claim 1, wherein the pouch includes an anti-microbial, liquid resistant fabric.

3. The male incontinence garment according to claim 1, further including a fastening device located on the flap and at a complimentary location on the undergarment.

4. The male incontinence garment according to claim 1, further including reinforcement around the aperture.

5. The male incontinence garment according to claim 1, wherein the pad further includes a material that contains moisture.

6. The male incontinence garment according to claim 1, wherein at least some length of the edges of the pad are heat sealed together to form the pocket.

7. The male incontinence garment according to claim 1, wherein the pad further includes a hole, wherein the penis passes through the hole into the pocket formed by the pad.

8. The male incontinence garment according to claim 1, wherein the pad and the adhesive are selectively removable from the pouch.

* * * * *